United States Patent [19]

Terada

[11] 4,329,980
[45] May 18, 1982

[54] FLEXIBLE SHEATH FOR AN ENDOSCOPE
[75] Inventor: Masaaki Terada, Hachioji, Japan
[73] Assignee: Olympus Optical Co., Ltd., Tokyo, Japan
[21] Appl. No.: 124,475
[22] Filed: Feb. 25, 1980
[30] Foreign Application Priority Data Mar. 6, 1979 [JP] Japan ................................. 54/25905

[51] Int. Cl.³ ........................................... A61B 1/00
[52] U.S. Cl. .................................. 128/4; 128/303.15
[58] Field of Search .................. 128/DIG. 9, 772, 4–8, 128/756, 757, 749, 349 R, 356, 348

[56] References Cited
U.S. PATENT DOCUMENTS

| 2,243,992 | 6/1941 | Wappler | 128/8 |
| 2,437,542 | 3/1948 | Krippendurf | 128/349 R |
| 3,500,820 | 3/1970 | Almen | 128/348 |
| 3,572,325 | 3/1971 | Bazell | |
| 3,854,473 | 12/1974 | Matsud | 128/8 |
| 3,948,251 | 4/1976 | Hosono | 128/6 |
| 4,054,128 | 10/1977 | Seufert et al. | 128/4 |
| 4,176,662 | 12/1979 | Frazer | 128/6 |
| 4,215,703 | 8/1980 | Willson | 128/772 |

FOREIGN PATENT DOCUMENTS

| 2059574 | 6/1971 | Fed. Rep. of Germany . |
| 2353893 | 5/1974 | Fed. Rep. of Germany . |
| 2758463 | 6/1978 | Fed. Rep. of Germany . |
| 50-13421 | 4/1975 | Japan | 128/4 |
| 52-316 | 1/1977 | Japan | 128/4 |
| 52-5194 | 1/1977 | Japan | 128/4 |
| 1153334 | 5/1969 | United Kingdom . |

Primary Examiner—Robert W. Michell
Assistant Examiner—Angela D. Sykes
Attorney, Agent, or Firm—Frishauf, Holtz, Goodman & Woodward

[57] ABSTRACT

A flexible sheath for an endoscope has a flexible hollow cylindrical tube and a helical coil spring which is inserted into the flexible hollow cylindrical tube. One end of the spring is made engageable with one end of the hollow cylindrical tube to adjust the flexibility of the flexible sheath. A mechanism for compressing the helical coil spring is provided at the other end of the hollow cylindrical tube. The mechanism comprises a spring-compressing member disposed at the other end of the helical coil spring and an actuating member for reciprocating the spring-compressing member between a position in which the spring-compressing member compresses the helical coil spring and a position in which the spring-compressing member is axially removed from the other end of the helical coil spring. The magnitude of a force axially applied to the helical coil spring is controlled in accordance with the extent to which the spring-compressing member is moved toward the helical coil spring by the actuating member, thereby adjusting the flexibility of the flexible sheath.

11 Claims, 15 Drawing Figures

FIG. 7A
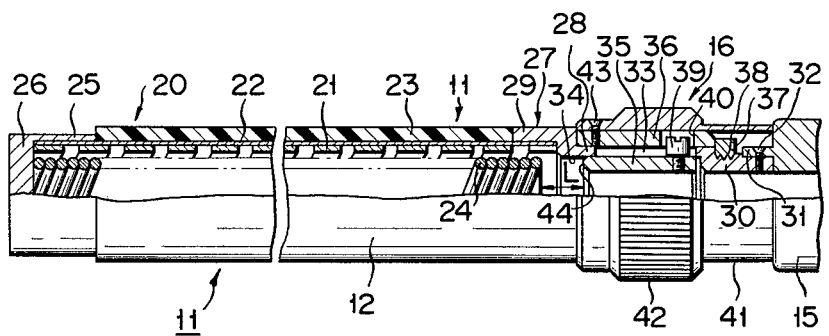
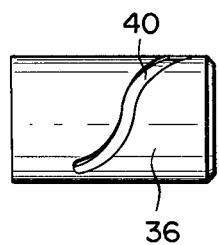
FIG. 7B
FIG. 8
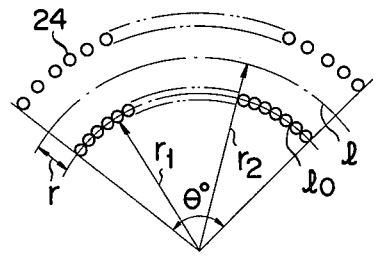

FLEXIBLE SHEATH FOR AN ENDOSCOPE

BACKGROUND OF THE INVENTION

This invention relates to a flexible sheath for an endoscope the flexibility of which can be freely adjusted.

An endoscope inserted into a narrow coeliac cavity such as the stomach, small intestine or large intestine comprises a flexible sheath allowing for the smooth insertion of said endoscope. However, the flexible sheath generally has its flexibility predetermined. Therefore, the difficulties have been encountered that, since an endoscope operator cannot adjust the flexibility of the flexible sheath to the physical condition of a coeliac cavity into which the flexible sheath is to be inserted, those parts of the coeliac cavity to which the endoscope is applicable are limited.

A colonoscope, a kind of endoscope, is now described. Referring to FIG. 1, a sigmoid colon 2 and a transverse colon 3 partly constituting a colon 1 are not fixed in position, but are readily moved in all ways through the abdominal cavity, and easily deformable. Therefore, a flexible sheath 4 of a colonoscope, put into the colon 1 from an anus 5 passes through the sigmoid colon 2 while being flexed along the inner wall thereof and finally reaches an outlet of the transverse colon 3. Where, however, it is tried to push the flexible sheath 4 beyond said outlet, the flexible sheath 4 is bent, failing to enter the transverse colon 3. Therefore, the conventional process comprises remotely controlling a bending section 6 formed at a distal end of the flexible sheath 4 by the angle control knob on the operation section of the colonoscope to divert the bending section 6 toward the transverse colon 3, holding the bending section 6 at the outlet of the transverse colon 3, thereafter pulling the colonoscope to make the flexible sheath 4 substantially straight as shown in FIG. 2, and again pushing the flexible sheath 4 into the transverse colon 3.

If, in this case, still remaining pliable, the flexible sheath 4 is easily bent when pushed again, even though previously straightened with effort, thus presenting difficulties in entering the transverse colon 3 and the preceding ascending colon.

To eliminate the above-mentioned drawbacks, it is attempted, as shown in FIG. 3, to insert a sliding tube 7 through which the flexible sheath 4 passes into the sigmoid colon 2 while letting the sliding tube 7 slide along the flexible sheath 4 after pushing the flexible sheath 4 up to the outlet of the transverse colon 3. This process prevents the flexible sheath 4 from being bent in the sigmoid colon 2, thereby enabling the flexible sheath 4 to be pushed into the transverse colon 3.

Even if the sliding tube 7 is applied, however, the flexible sheath 4 is bent in the transverse colon 3 all the same. Where, therefore, the flexible sheath 4 is further pushed into the transverse colon 3, the transverse colon 3 which should normally be kept in a horizontal position is pushed downward as shown in FIG. 3 into a U-shape. As a result, a patient feels a considerable pain. Moreover, the flexible sheath 4 has to be elongated by the length of the sliding tube 7, presenting difficulties in operating the colonoscope. Further, that portion of the colonoscope which is surrounded by the sliding tube 7 unavoidably has a larger diameter. This goes contrary to the requirement for the colonoscope to be made as narrow as possible.

Apart from the above-mentioned attempt, it may be contemplated to originally render the forward end portion of the sheath 4 of the colonoscope flexible and the remaining portion of the sheath 4 more rigid than the forward end portion thereof. In this case, the flexible forward end portion of the sheath 4, if made long, can indeed be easily inserted into the sigmoid colon 2 without giving pain to a patient. However, when the colonoscope is tried to be further inserted, the flexible forward portion is bent thereby to meander the sigmoid colon 2 as shown by broken lines in FIG. 4. Conversely, where the flexible foward end portion of the sheath 4 is made short, the sheath 4 lifts the sigmoid colon 2 as shown by chain lines in FIG. 5, if the sheath 4 is further inserted. Eventually, the patient suffers a considerable pain.

To resolve the above-mentioned difficulties, a colonoscope has been proposed which comprises a flexible sheath whose flexibility can be varied, as need arises. Already known is, for example, that type of colonoscope, whose flexible sheath comprises an extendible and contractible tube assembly which is formed of a pair of helical coils. These coils are made by winding metallic belts. One of them is inserted into the other. The turns of both the coils are directed reversely to each other. The assembly is moved through the flexible sheath, thereby adjusting the flexibility of said flexible sheath.

Where, however, an elongate flexible sheath of a colonoscope is made of the above-mentioned type, the extendible and contractible tube assembly has to be moved axially for a considerable distance in order to vary the physical condition of the flexible sheath from the freely flexible state to the rigid condition. As a result, the operation section of the colonoscope is elongated, presenting difficulties in handling the colonoscope. Moreover, the assembly is not always moved uniformly over its entire length. Especially, the distal end portion of the assembly is moved less than its proximal end portion and its intermediate portion. Thus, the flexible sheath tends to bend unevenly. Where, to avoid such drawbacks, the turns of the extendible and contractible tubes are coiled at a small pitch, then the flexible sheath cannot have a small redius of curvature even when the flexible sheath is in a freely flexible state. Moreover, where a coeliac cavity has intricate distortions like those of a large intestine, the flexible sheath of the above-mentioned known type of colonoscope which comprises an extendible and contractible tube assembly fails to closely follow such intricate bending.

Another proposed colonoscope is the type whose flexible sheath comprises a wave-shaped spring ring assembly and a plurality of pull wires. The spring ring assembly consists of a row of plurality of wave-shaped spring rings. Each ring except for the rearmost ring has its wave troughs pressed against the wave crests of the adjacent ring such that they form junctions. Each of the pull wires has its distal end fixed to the corresponding junction of the foremost pair of rings and passes through the respective junctions of other pairs of the rings. According to said another proposed colonoscope, the flexible sheath indeed has its flexibility adjusted in accordance with the extent to which the respective pull wires are pulled toward the proximal end of the colonoscope. But said proposed colonoscope has the drawbacks that where an external stress is applied to the peripheral wall of the flexible sheath, said flexible sheath is not bent arcuately but possibly meanders; when the colonoscope is repeatedly used, the wires passing through the flexible sheath tend to be broken;

and since flexible sheath itself is rendered extendible and contractible, the optical fiber bundles passing through said sheath are likely to be damaged under a tensile force or compression force.

Still another colonoscope is the type which comprises a plurality of wires axially passing therethrough, and wherein one end of each of the wires is fixed to the distal end of the flexible sheath and the other end thereof is fixed in the operation section of the colonoscope. The respective wires pass through the corresponding coil springs, and the flexibility of the flexible sheath is adjusted by pushing the coil springs at the other ends of the wires.

With the above-mentioned type of colonoscope, it is difficult to provide the coil springs, all of which have the same spring characteristics. Where, therefore, the coil springs are pushed to render the flexible sheath rigid, the flexible sheath is irregularly bent. Further, where the flexible sheath is bent, the wires passing through the flexible sheath are not bent in the same degree as the flexible sheath, but tend to be straightened. As a result, the wires partly strike or rub optical fiber bundles passing through the flexible sheath and the inner wall thereof, probably leading to the damage of the fiber bundles and inner wall, and consequently are ready to be broken.

An object of this invention is to provide a compact endoscope flexible sheath, whose flexibility can be adjusted easily and unfailingly as need arises in an elongate intricately twisted coeliac cavity, and which can be inserted into the depth of the coeliac cavity without imparting pains to the patient.

Another object of the invention is to provide an endoscope flexible sheath, wherein a maximum rigidity is predetermined for the respective sections of the flexible sheath, thereby enabling the overall flexibility of said flexible sheath to be varied as need arises in conformity to the internal physical condition of a coeliac cavity.

SUMMARY OF THE INVENTION

An endoscope flexible sheath embodying this invention comprises a flexible hollow cylindrical tube and a single helical coil spring, one end of which is engageable with one end of the hollow cylinrical tube, thereby adjusting the flexibility of the flexible sheath. A helical coil spring-compressing mechanism provided at the other end of the hollow cylindrical tube comprises a pressing member engaged with the other end of the single helical coil spring and an actuating section for reciprocating the spring-compressing member between a position in which the spring-compressing member pushes the single helical coil spring and a position in which the spring-compressing member is axially removed from the other end of the single helical coil spring. The flexible sheath of the invention can have its flexibility varied by controlling the magnitude of a force axially applied to the single helical coil spring in accordance with the extent to which the spring-compressing member is pushed toward the single helical coil spring by the actuating member.

At least one abutment is provided at an intermediate part of the inner wall of the hollow cylindrical tube. A stop is formed on the peripheral wall of that part of the helical coil spring which lies near the other end thereof in proximity to the abutment for engagement therewith. Where the stop is engaged with the abutment when the helical coil spring is compressed by the compressing member, that part of the helical coil spring which lies beyond the stop is prevented from being subjected to a force greater than that with which said part of the helical coil spring is compressed. This arrangement enables that part of the flexible sheath which lies beyond the abutment to be formed of a more flexible material than that part of the flexible sheath which lies behind the abutment.

BRIEF DESCRIPTION OF THE DRAWING

FIG. 7A is a longitudinal sectional view of an endoscope flexible sheath according to one embodiment of the invention;

FIG. 7B is a side view of a slider included in FIG. 7A;

FIG. 8 shows the action of a helical coil spring used with the embodiment of FIG. 7;

DETAILED DESCRIPTION

A flexible sheath embodying this invention is adapted for use with an endoscope which is inserted into a coeliac cavity such as the stomach, small intestine and large intestine and requires an elongate flexible sheath, and particularly with such endoscope as is inserted into an elongate, intricately twisted coeliac cavity like the large intestine.

Figure 1:
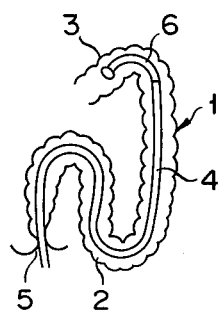
FIGS. 1 to 5 illustrate the operation of the known flexible sheath for an endoscope.
Figure 2:
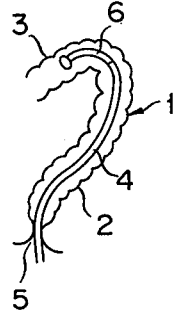
Figure 3:
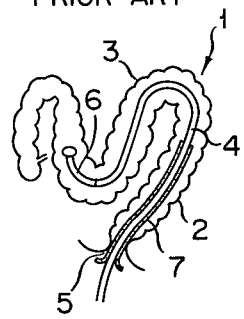
Figure 4:
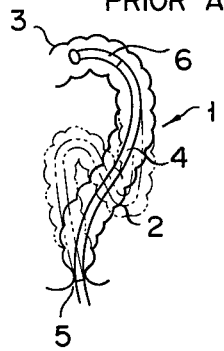
Figure 5:
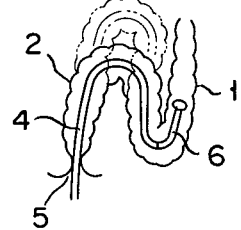
Figure 6:
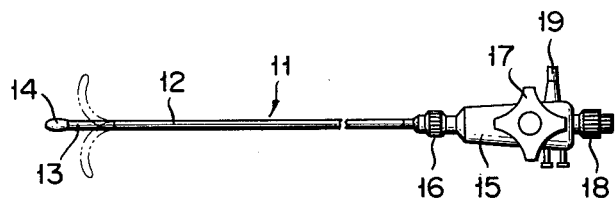
FIG. 6 is a front view of an endoscope provided with a flexible sheath based on this invention.

FIG. 6 shows an endoscope 11 provided with an elongate flexible sheath 12 embodying this invention. The endoscope 11 comprises the elongate flexible sheath 12, a bending section 13 which is fixed to one end of the flexible sheath 12 and at whose forward end a distal end section 14 of the endoscope 11 is disposed, and an operation section 15 connected to the other end of the flexible sheath 12 by means of a helical coil spring-compressing mechanism 16. An angle-adjusting knob 17 mounted on one lateral wall of the operation section 15 enables the bending section 13 to be bent by wires extending through the sheath 12 in any direction and at any curvature as shown in chain lines in FIG. 6 as in the case of the conventional endoscope. The endoscope 11 comprises an axially penetrating observation optical fiber bundle, one end of which is connected to an eyepiece 18 disposed at the proximal end of the endoscope 11, and the other end of which is optically connected to an objective lens received in the distal end section 14 of the endoscope 11; and a similarly axially penetrating illumination optical fiber bundle, one end of which is connected to an illumination window opened in the distal end section 14 of the endoscope, and the other end of which is optically connected to a light source through a connector tube 19 extending outward from the lateral wall of the operation section 15 of the endoscope 11. Further, a channel or channels allowing for the run of a fluid such as air, medical liquid and water pass through the endoscope 11. In addition to the above-mentioned parts, the endoscope 11 comprises the same parts as those of the known endoscope. However, these parts fall outside of the object of this invention, description thereof being omitted.

The endoscope flexible sheath 12 shown in FIG. 7A comprises a flexible cylindrical tube 20 formed of a helical tube 21 constructed by winding a strip of belt-shaped elastic metal (for example, stainless steel or phosphor bronze), a braid or net tube 22 of stainless steel or brass tightly surrounding the helical tube 21, and a flexible outer tube 23 of plastic material such as urethane resin closely enveloping said braid or net tube 22. The helical tube 21 and net tube 22 respectively suppress the radial deformation and elongation of the flexible sheath 12. On the other hand, the flexible outer tube 23 allows for the bending of the flexible sheath 12.

Inserted into the flexible cylindrical tube 20 is a helical coil spring 24 having an outer diameter about 0.2 to 0.3 millimeter smaller than the inner diameter of the helical tube 21 for the adjustment of the flexibility of the flexible sheath 12. This helical coil spring 24 is constructed by winding a wire of elastic metal such as spring steel with the respective turns of the coil spaced from each other as slightly as, for example, 0.02 to 0.2 millimeter.

A hollow cylindrical block 25 is fixed to the distal end of the flexible cylindrical tube 20. A flange-shaped spring seat 26 is formed at the distal end of the block 25. The distal end of the helical coil spring 24 is pressed against the flange-shaped spring seat 26.

A connector tube 27 comprises a hollow cylindrical body 28, a large diameter flange section 29 formed at one end of the hollow cylindrical body 28 to fix the proximal end of the flexible cylindrical tube 20, and a cylindrical end section 30 formed at the other end of the flange section 29 with a smaller diameter than that of the hollow cylindrical body 28. The cylindrical end section 30 of the connector tube 27 is fixed to a fitting flange 31 provided at the distal end of the operation section 15 of the endoscope 11 by means of screws 32. A long axially extending guide groove 33 is formed in the body 28 of the connector tube 27.

A hollow cylindrical slider 35 is inserted into the connector tube 27 so as to slide on the inner peripheral wall 34 thereof. A hollow cylindrical actuating member 36 is fitted into the body 28 of the connector tube 27. This hollow cylindrical actuating member 36 is prevented from being axially moved by a nut 37 threadedly engaged with a male screw formed in the outer peripheral wall of the cylindrical end section 30 of the connector tube 27. An outward projecting pin 39 fixed to the outer peripheral wall of the hollow cylindrical slider 35 is engaged with a helical groove 40 formed in the wall of the hollow cylindrical member 36 (FIG. 7B).

A rotary ring 41 extends from the flange 29 to the distal end of the operation section 15 of the endoscope 11. This rotary ring 41 has a larger diameter knurled ring portion 42 formed in the intermediate part and is fixed to the hollow cylindrical member 36 by means of a screw or screws 43. Where the slider 35 is retracted most backward, the distal end plane 44 of the slider 35 is removed from the helical coil spring 24 for a distance of L taken as a maximum clearance. The connector tube 27, slider 35, hollow cylindrical actuating member 36, nut 37 and rotary ring 41 collectively constitute the helical coil spring-compressing mechanism 16.

In operation, where the rotary ring 41 is rotated to the right side or clockwise as viewed from the operation section 15 of the endoscope 11, the outward projecting pin 39 is moved toward the flexible tube 12 by the guidance of the groove 40 of the actuating member 36 in the guide groove 33 formed in the body 28 of the connector tube 27. As a result, the slider 35 is moved toward the flexible sheath 12, causing the distal end plane 44 of the slider 35 to press the proximal end of the helical coil spring 24 for compression. The extent to which the helical coil spring 24 is to be compressed is defined in accordance with the extent to which the rotary ring 41 is rotated, thereby controlling the flexibility of the flexible sheath 12. The more extensive the clockwise rotation of the rotary ring 41, the greater the compression of the helical coil spring 24. Accordingly, the flexible sheath 12 becomes more rigid and is less likely to be bent. Obviously, the clearance L need not be restrictively provided between the helical coil spring 24 and the slider 35, but instead may be formed between the distal end of the helical coil spring 24 and the spring seat 26 of the spring rest 25. In this case, it is advised to fix the proximal end of the helical coil spring 24 to the distal end plane 44 of the slider 35.

While the helical coil spring 24 is not compressed by the slider 35, the flexible sheath 12 remains most flexible, and is easily bent in accordance with the shape of the coeliac cavity into which the flexible sheath 12 is inserted. If, therefore, selection is made between the process of preventing the helical coil spring 24 from being compressed by the slider 35 and the process of properly compressing the helical coil spring 24 to render the flexible sheath 12 suitably rigid, the flexible sheath 12 can be inserted more deeply and smoothly into the coeliac cavity than has been possible in the past, without letting the patient feel an unnecessary pain.

As previously described, the turns of the helical coil spring 24 are very slightly spaced from each other. For briefness of description, however, the respective turns of the helical coil spring 24 are supposed to be tightly contact each other by disregarding the inter-turn space. In this case, the free length of the helical coil spring 24 is expressed as $l_0$. Where the helical coil spring 12 is not compressed by the slider 35, the minimum radii of curvature of the inner wall of the bent portions of the respective turns of the helical coil spring 24 and the axial line of the bent portions of the helical coil spring 24 are represented by $r_1$, $r_2$. The length of the helical coil spring 24 along the axial line is denoted by l. A maximum angle defined by the center of curvature and both ends of the helical coil spring 24 bent during the insertion of the flexible sheath 12 into a coeliac cavity is taken to be $\theta°$. Then the length of the inner wall of the bent helical coil spring 24 is $l_0$ (see FIG. 8). Accordingly, the following equation results.

$$l - l_0 = 2\pi(r_2 - r_1)(\theta°/360°) \tag{1}$$

where the term $(r_2 - r_1)$ denotes the radius r of the bent helical coil spring 24. Assuming that the term $(l - l_0)$ is equal to the clearance L, then the following equation results.

$$L = \pi r \theta°/180° \tag{2}$$

Therefore, r and $\theta°$ are defined in accordance with the shape of the coeliac cavity into which the flexible sheath 12 is inserted, and the clearance L is determined from the equation (2).

When inserted into the large intestine, the flexible sheath 12 is chosen to have the following dimensions.

Length of the flexible sheath 12—

Figure 9:
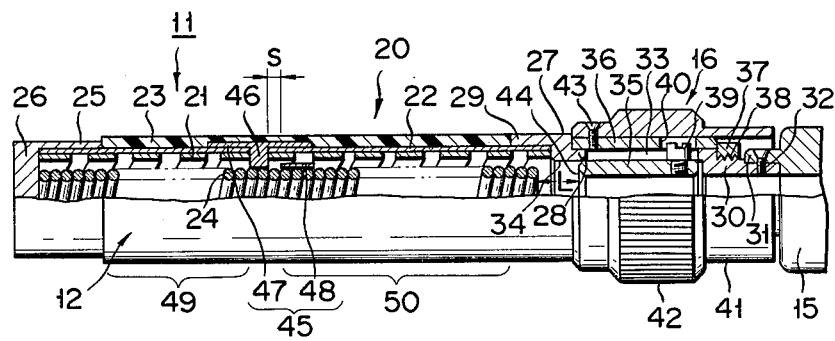
FIG. 9 is a longitudinal sectional view of an endoscope flexible sheath according to another embodiment of the invention.

1,600 millimeters (maximum)
Outer diameter of the flexible sheath 12—
 16 millimeters
Inner diameter of the flexible sheath 12—
 13 millimeters
Diameter of the strand of the helical coil spring 24—
 0.8 to 1.2 millimeters
Outer diameter of the helical coil spring 24—
 12.5 millimeters
Length of the helical coil spring 24—
 1,500 millimeters
Clearance L—
 30 to 50 millimeters A flexible sheath according to the embodiment of FIG. 9 is modified from that of FIG. 7A by additionally providing a mechanism 45 for varying the flexibility of the flexible sheath 12. The flexibility-varying mechanism 45 comprises a cylindrical member 47 which has an inwardly projecting annular abutment 46 formed at the center and is embedded in the outer tube 23, and a ring-shaped stop 48, which is fixedly mounted on the helical coil spring 24 and, when the helical coil spring 24 is not compressed by the slider 35, is spaced at an interval of s (5 to 10 millimeters) from the annular abutment 46 toward the operation section 15 of the endoscope 11. The arrangement of the other parts of the embodiment of FIG. 9 is the same as that of FIG. 7A.

Where the helical coil spring 24 is compressed by the slider 35 at the rotation of the rotary ring 41, the helical coil spring 24 is uniformly compressed, until the stop 48 is pressed against the abutment 46. Therefore, the flexible sheath 12 has its rigidity or flexibility adjusted in accordance with the extent to which the helical coil spring 24 is compressed by the slider 35. After, however, the stop 48 contacts the abutment 46, that portion of the helical coil spring 24 which extends from the stop 48 to the distal end of the spring 24 is not compressed beyond the extent to which the other portion of the helical coil spring 24 was previously compressed by the movement of the slider 35 toward the block 25. Thus, only that portion of the helical coil spring 24 which extends from the stop 48 to the proximal end of the spring 24 is further compressed. Therefore, the flexible sheath 46 according to the embodiment of FIG. 9 can have its physical condition varied in two stages. Namely, that portion of the flexible sheath 12 which extends from the abutment 46 to the distal end of said sheath 12 that is, the forward half section 49 of the sheath 12 is rendered rigid to such an extent that the spring 24 is exerted with the compressive force when the stop 48 engages the abutment 46. In contrast, that portion of the flexible sheath 12 which extends from the abutment 46 to the proximal end of the sheath 12, namely, the rear half section 50 of the sheath 12 is rendered more rigid, according as the helical coil spring 24 is more compressed.

Description is now given of the case where an endoscope provided with the flexible sheath 12 of FIG. 9 is used as a colonoscope.

Figure 10:
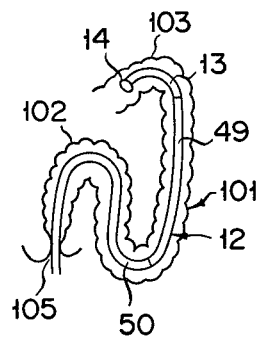
FIGS. 10 to 12 show the operation of the flexible sheath of FIG. 9.
Figure 11:
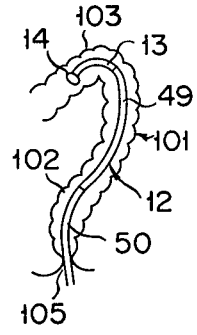
Figure 12:
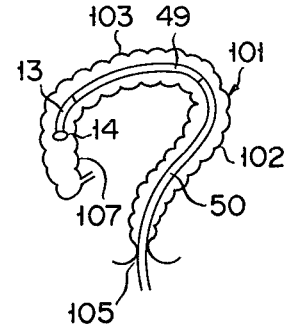

Referring to FIG. 10, the colonoscope is inserted from the anus 105 into the large intestine 101 through the sigmoid colon 102 with the flexible sheath 12 left free, until the distal end section 14 of the flexible sheath 12 is brought to the outlet of the transverse colon 103. Thereafter, the bending section 13 of the flexible sheath 12 is bent by the angle-adjusting knob 17 so as to cause the distal end section 14 of the endoscope 11 to be directed to the transverse colon 103, thereby holding the distal end section 14 of the endoscope 11 at the outlet of the transverse colon 103. Thereafter, as shown in FIG. 11, the flexible sheath 12 is pulled backward to straighten the sigmoid colon 102. Next, the rotary ring 41 is rotated to fully compress the helical coil spring 24, thereby rendering the flexible sheath 12 rigid. Since, at this time, the rear half section 50 of the flexible sheath 12 is rendered fully rigid, the flexible sheath 12 can be inserted into the sigmoid colon 102 without being bent. On the other hand, the forward half section 49 of the flexible sheath 12 is rendered appreciably more flexible than the rear half section 50. When, therefore, the flexible sheath 12 is inserted into the transverse colon 103, the forward half section 49 is bent in accordance with the shape of the transverse colon 103. The forward half section 49 of the flexible sheath 12 is guided, as shown in FIG. 12, through the transverse colon 103 up to the ascending colon 107 without pushing up or forcing down the transverse colon 103. Consequently, the flexible sheath 12 according to the embodiment of FIG. 9 smoothly enter the large intestine 101 without imparting a considerable pain to the patient.

The flexible sheath 12 of FIG. 9 comprises a single flexibility-varying mechanism 45. However, a plurality of flexibility-varying mechanisms 45 may be provided to render that portion of the flexible sheath 12 which lies nearer to the distal end section thereof more flexible. In this case, the interval s between the ring-shaped stop 48 and annular abutment 46 is obviously made narrower toward the distal end section of the flexible sheath 12.

Figure 13:
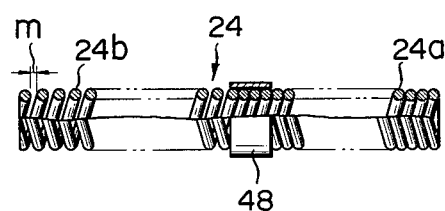
FIGS. 13 and 14 are longitudinal sectional views of an endoscope flexible sheath according to other embodiments of the invention.

FIG. 13 shows a modification of the helical coil spring 24. The rear half section 24a of the spring 24 extending from the stop 48 to the proximal end of the spring 24 is formed of substantially tightly wound turns as in the helical coil springs shown in FIGS. 7A and 9. The forward half section 24b of the spring 24 extending between the stop 48 and the distal end section of the spring 24 is formed of turns wound at an interval of m (0.1 to 0.3 millimeter when the endoscope is used as a colonoscope). The forward half section 24b of the helical coil spring 24 thus constructed has a smaller mechanical strength than the forward half section of the helical coil spring of FIG. 9, thereby enabling the forward half section 24b of the flexible sheath 12 of FIG. 13 to be more easily bent.

Figure 14:
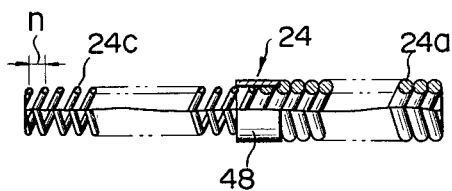

With a helical coil spring 24 according to the embodiment of FIG. 14, the rear half section 24a which extends from the stop 48 to the proximal end is of the same construction as the rear half section 24a of the helical coil spring 24 according to the embodiment of FIG. 13. However, the forward half section 24c of the helical coil spring 24 according to the embodiment of FIG. 14 has an outer diameter of, for example, 12 millimeters and is mechanically weaker (that is, formed of spring steel strands having a diameter of, for example, 0.3 to 0.7 millimeter) and has the respective turns spaced from each other at an interval of n (for example, 0.3 to 0.7 millimeter). Therefore, the forward half section 24c of a flexible sheath containing the helical coil spring 24 according to the embodiment of FIG. 14 has a higher flexibility than the forward half section 24b of a flexible sheath containing the helical coil spring 24 of FIG. 13.

What is claimed is:

1. A flexible sheath arrangement for an endoscope comprising:
 a flexible hollow cylindrical tube having two ends; and a single helical coil spring inserted into the flexible hollow cylindrical tube and forming with said hollow cylindrical tube the outer sheath of the endoscope, the single helical coil spring having two ends and an intermediate part between said two ends, one end of the helical coil spring being engageable with one end of the hollow cylindrical tube for adjusting the flexibility of the hollow cylindrical tube;

a helical coil spring-compressing means provided at the other end of the hollow cylindrical tube for urging the helical coil spring toward said one end of the hollow cylindrical tube by pressing against the other end of the helical coil spring;

engaging means provided in said hollow cylindrical tube for holding said intermediate part of the helical coil spring and comprising at least one abutment formed on said hollow cylindrical member and extending inward therefrom; and a stop fixedly mounted on a portion of said helical coil spring which is adjacent to said abutment and remote from said one end of the hollow cylindrical tube with respect to said abutment, for engaging said abutment when said helical coil spring is compressed;

a first clearance formed between said other end of the helical coil spring and the helical coil spring-compressing means; and a second clearance narrower than said first clearance and provided between the abutment and the stop.

2. The flexible sheath arrangement according to claim 1, wherein said single helical coil spring comprises a first section between said stop and said other end of the helical coil spring having turns substantially tightly contacting each other and a second section between said stop and said one end of the helical coil spring having turns spaced from each other at a broader interval than said turns of the first section of the helical coil spring.

3. The flexible sheath arrangement according to claim 1, wherein said single helical coil spring comprises a first section between said stop and said other end of the helical coil spring having turns substantially tightly contacting each other, and a second section extending between the stop and said one end of the helical coil spring formed of a mechanically weaker helical coil spring material than the first section.

4. The flexible sheath arrangement according to claim 1, wherein said single helical coil spring comprises a first section between said helical coil spring-compressing means and said other end of the helical coil spring having turns substantially tightly contacting each other, and a second section between said helical coil spring-compressing means and said one end of the helical coil spring having coarse turns.

5. The flexible sheath arrangement according to claim 1, wherein said single helical coil spring comprises a first section between said helical coil spring-compressing means and said other end of the helical coil spring having turns substantially contacting each other, and a second section between said helical coil spring-compressing means and said one end of the helical coil spring comprising a mechanically weaker helical coil spring material than the first section.

6. The flexible sheath arrangement according to claim 1, wherein said single helical coil spring-compressing means comprises:
a connector tube fixed at said other end of the hollow cylindrical tube;
a slider slidably fitted into the connector tube for urging said helical coil spring toward said one end of said one end of said hollow cylindrical tube; and
a pushing mechanism for pushing the slider toward the helical coil spring.

7. The flexible sheath arrangement according to claim 6, wherein the slider is spaced from the helical coil spring at a prescribed interval.

8. The flexible sheath arrangement according to claim 6, wherein the slider-pushing mechanism comprises:
a hollow cylindrical actuating member rotatable around said connector tube and having an outer peripheral wall provided with a helical groove;
a guide groove formed in said connector tube and extending axially thereof;
a pin fixedly mounted on said slider and inserted into the helical groove and the guide groove; and
a rotary ring fixedly mounted on the hollow cylindrical actuating member and rotated to reciprocate said slider for compressing said helical coil spring and thus adjusting flexibility of the flexible sheath.

9. The flexible sheath arrangement according to claim 1, wherein said abutment is an annular member.

10. The flexible sheath for an endoscope according to claim 9, wherein the stop is a ring-shaped member.

11. The flexible sheath according to claim 1, wherein said single helical coil spring is formed of turns substantially tightly contacting each other.

* * * * *

UNITED STATES PATENT AND TRADEMARK OFFICE
CERTIFICATE OF CORRECTION

PATENT NO. : 4,329,980
DATED : May 18, 1982
INVENTOR(S) : Massaki TERADA

It is certified that error appears in the above—identified patent and that said Letters Patent is hereby corrected as shown below:

In the heading of the patent, under the title of "Foreign Application Priority Data", insert the following:

--Mar. 6, 1979 [JP]   Japan..............54/25906--.

Signed and Sealed this

Twenty-fourth Day of August 1982

|SEAL|

Attest:

GERALD J. MOSSINGHOFF

Attesting Officer    Commissioner of Patents and Trademarks